United States Patent
T

(10) Patent No.: US 11,779,215 B2
(45) Date of Patent: Oct. 10, 2023

(54) ENHANCED ECG WORKFLOWS

(71) Applicant: GE Precision Healthcare LLC, Wauwatosa, WI (US)

(72) Inventor: Satyanarayana T, Bangalore (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 203 days.

(21) Appl. No.: 16/820,908

(22) Filed: Mar. 17, 2020

(65) Prior Publication Data

US 2021/0290061 A1    Sep. 23, 2021

(51) Int. Cl.
*A61B 5/00* (2006.01)
*G16H 40/67* (2018.01)
*G16H 50/70* (2018.01)
*A61B 5/364* (2021.01)

(52) U.S. Cl.
CPC ............ *A61B 5/0006* (2013.01); *A61B 5/364* (2021.01); *A61B 5/7264* (2013.01); *A61B 5/7285* (2013.01); *G16H 40/67* (2018.01); *G16H 50/70* (2018.01)

(58) Field of Classification Search
CPC ..... A61B 5/0006; A61B 5/364; A61B 5/7264; A61B 5/7285; G16H 15/00; G16H 40/63; G16H 40/67; G16H 50/20; G16H 50/70
See application file for complete search history.

(56) References Cited

U.S. PATENT DOCUMENTS

| 2007/0255337 A1* | 11/2007 | Lu ...................... A61N 1/36007 607/40 |
| 2013/0158423 A1* | 6/2013 | Kapoor .............. A61B 5/02405 600/523 |
| 2013/0282405 A1 | 10/2013 | Van Zon et al. |
| 2015/0265164 A1* | 9/2015 | Gopalakrishnan ... A61B 5/7264 600/513 |
| 2016/0135706 A1* | 5/2016 | Sullivan ................. A61B 5/316 600/509 |
| 2019/0198169 A1 | 6/2019 | T et al. |

FOREIGN PATENT DOCUMENTS

CN          101346722 A     1/2009

* cited by examiner

*Primary Examiner* — George Manuel

(57) ABSTRACT

A method and system for obtaining and analyzing ECG waveforms from a patient is disclosed. Initially, a recommendation for obtaining an ECG waveform from a patient is issued, typically from a cardiologist. An ECG recording device is used to obtain ECG data from the patient. The recording device generates patient identification information, time and date information and an initial analysis that are included in a log delivered along with the ECG data to an analysis server. The analysis server generates a recommended action for the patient, which is delivered to the recording device while the patient is still present at the recording device. The recording device can then carry out the recommended action and provide the results for analysis by the cardiologist. The analysis server can utilize artificial intelligence/machine learning to generate the recommended action for the patient without having to involve the cardiologist, thereby reducing the number of visits for the treatment of the patient.

17 Claims, 7 Drawing Sheets

ENHANCED ECG WORKFLOWS

BACKGROUND

The present disclosure generally relates to improvements in workflows done in the analysis of ECG waveforms obtained from a patient. More specifically, the present disclosure relates to enhancement of the ECG workflow by doing analysis of user actions on a recording device for each of the patients and providing recommendation for any further analysis while the patient is present at the recording device to reduce time for early treatment plans.

BRIEF DISCLOSURE

Presently, the typical ECG workflows are done offline based on the recommendation of a cardiologist. The typical workflow includes the initial step of the patient detecting some problem and going to a cardiologist for a visit. After initially seeing the cardiologist, the cardiologist typically recommends a 10 sec resting ECG for initial analysis. After the resting ECG is recommended for the patient at the initial visit with the cardiologist, the patient goes to a diagnostic center (either the same hospital or a separate diagnostic center like in developing countries) to take the ECG reading.

At the diagnostic center, a trained technician takes the ECG measurements from the patient and gives the measurements to the patient or updates ECG measurement information online. After receiving the measurements, the patient typically returns to the cardiologist and the cardiologist checks for ECG abnormalities. If the cardiologist observes some type of abnormality in the ECG, such as an arrhythmia, the cardiologist recommends further analysis for the patient. For example, the cardiologist may recommend a "Hi-Res"/ "30 min Of Rhythm"/"Stress ECG" for the patient.

As a result of this analysis of the initial ECG measurement, the patient must return to the technician and get the cardiologist recommended ECG taken. After this second ECG, the patient again returns to the cardiologist and the cardiologist reviews the second ECG and recommends treatment for the patient.

The inventors of the present disclosure have identified problems with this current workflow and have developed the present disclosure to enhance and improve on the state of the art. The present disclosure describes enhancement of this workflow by doing analysis of user actions on a recording device for patients and provide recommendation for any further analysis while the patient is still at the recording device to reduce time for treatment.

The enhanced workflow in accordance with the present disclosure includes the initial step of the patient detecting some problem and going to the cardiologist. The cardiologist will then typically recommend a 10 sec resting ECG for initial analysis. As in the past workflow set forth above, the patient then goes to a diagnostic center (either the same hospital or a diagnostic center) to take ECG reading.

After the initial ECG reading is obtained from the patient, the initial ECG reading from the patient is analyzed either at the recording device or by a remote serve and the technician received a recommendation while the patient is still present at the ECG recording device. For example, the recommendation may be to further take "30 min rhythm"/"Hi-Res"/ "Stress ECG". The recommendation could include other ECG recording formats depending on the patient and the analysis. Since this recommendation is received while the patient is still present at the recording device, the technician can obtain the enhanced ECG recording and can give a full, detailed recording to the patient or can upload the information to a data network.

After leaving the diagnostic center, the patient can visit a cardiologist and the cardiologist can review the enhanced ECG waveform for abnormalities and can recommend treatment. Such enhanced workflow eliminates the intermediate visits with the cardiologist as in the prior art workflow described above.

As a result of the present disclosure, the system and method can develop an early treatment plan for the patient as compared to the workflow of the prior art. This reduction in time is due to the elimination of the back and forth between the ECG technician and the cardiologist. Further, a proper detailed ECG can be recorded the first time the patient meets with the ECG technician, even if the technician has less expertise and experience, which is common in diagnostic center. Finally, the present disclosure provides enhanced analysis by the combination of multiple ECG recording workflow is made possible.

DETAILED DISCLOSURE

Figure 1:
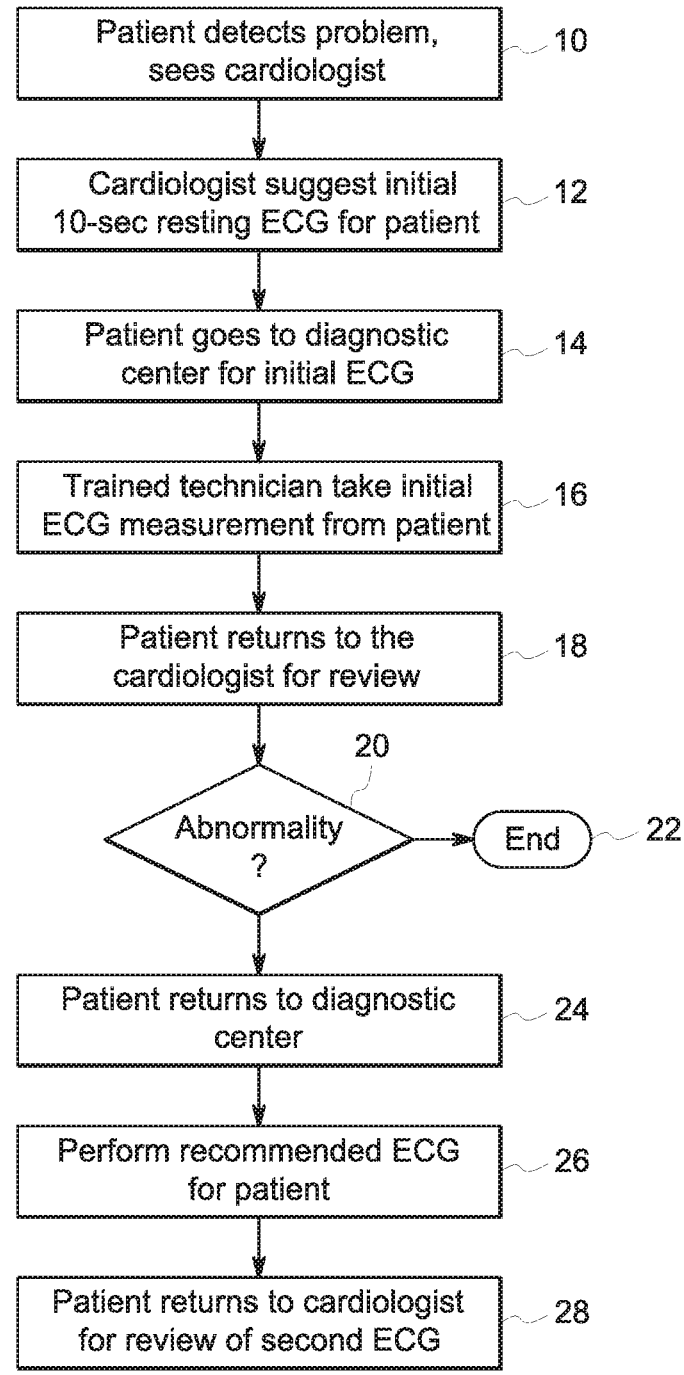
FIG. 1 is a flow chart depicting a prior art workflow in obtaining ECG and analizing ECG waveforms from a patient.

FIG. 1 illustrates the prior art, typical workflow done in obtaining ECG waveforms from a patient and the steps necessary to perform the proper analysis of the ECG waveform by a cardiologist. As indicated in step 10, the patient and/or health care professional initially detects some sort of health problem and travels to an initial visit with a cardiologist. Initially, in step 20, the cardiologist meets with the patient and, based upon the initial meeting, suggests an initial ECG recording, such as a ten second resting ECG, in step 12. The ten second resting ECG can be used by the cardiologist to initially provide limited diagnostic information relative to cardiac health of the patient.

After the cardiologist suggests the resting ECG in step 12, the patient travels to a diagnostic center, which may be the same hospital where the patient met with the cardiologist or may be a separate diagnostic center, as is the case in developing countries. After reaching the diagnostic center, as illustrated in step 14, a technician at the diagnostic center takes the ECG measurement from the patient in step 16. In many cases, the technician may be trained only on how to operate the ECG recording device and may not be able to make any type of initial diagnosis based on the ECG measurement. Such is the case in many developing countries.

After the initial ECG measurement has been taken from the patient, the technician either provides the information to the patient in an electronic form or uploads the recorded information to an electronic site that is accessible by the cardiologist. After the initial ECG measurement has been taken in step 16, the patient returns to the cardiologist in step 18. While at the cardiologist for the second visit, the cardiologist can review the ECG recording and can check for ECG abnormalities in step 20. If no abnormalities are detected, the cardiologist provides this information to the patient in step 22 and the analysis is complete.

However, if the cardiologist determines in step 20 that abnormalities are present in the ECG recording in step 20, the cardiologist recommends that further analysis be carried out and that additional ECG information should be obtained from the patient. As an example, the cardiologist may recommend that a Hi-Res ECG or a stress induced ECG be performed for the patient. The recommendation is not limited to the exemplary report types and could include any other ECG report. To get this type of testing done, the patient returns to the diagnostic center, as illustrated by step 24. At the diagnostic center, the recommended ECG for the patient is obtained by the trained technician as illustrated in step 26. After this second, recommended ECG is taken, the ECG recording is again either given to the patient or uploaded for viewing by the cardiologist. After this second ECG recording is taken for the patient, the patient again returns to the cardiologist for a third visit in step 26, where the cardiologist can then perform a more full and complete analysis of the recommended ECG that was taken in step 26.

As can be understood by the prior art workflow illustrated in FIG. 1, the patient typically needs to return to the diagnostic center and cardiologist multiple times depending upon whether the cardiologist detects abnormalities in the initial ECG waveform following the initial ECG reading. The inventors of the present disclosure have identified the problems associated with the current workflow shown in FIG. 1 and have developed the present disclosure to enhance and improve upon the workflow shown in FIG. 1.

Figure 2:
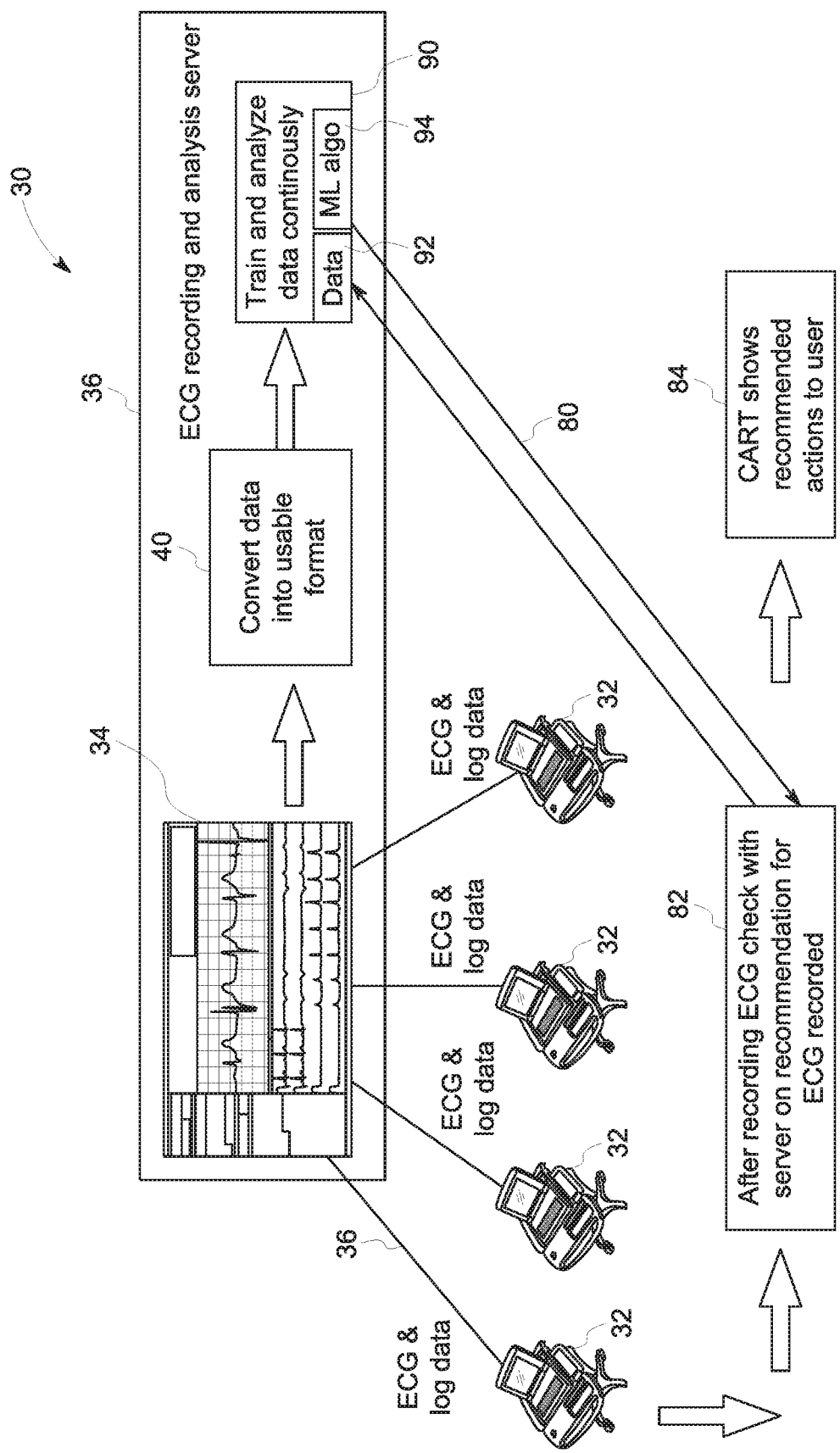
FIG. 2 is a schematic diagram of a ECG workflow in accordance with an exemplary embodiment of the present disclosure.

FIG. 2 is a schematic illustration of the workflow 30 carried out in accordance with the present disclosure. As illustrated in FIG. 2, multiple ECG recording devices 32 can be located at a diagnostic center and each can be used to obtain ECG waveforms from a patient. Each of the ECG recording devices 32 are commonly known ECG recording devices that can be utilized to obtain ECG waveforms from a patient. In FIG. 2, the ECG waveform data obtained from the patient is illustrated by the ECG information display 34. In accordance with the present disclosure, once the ECG waveform data has been obtained from the patient, each of the individual ECG recording devices 32 can communicate the obtained ECG waveform information to an analysis server 36. The ECG analysis server 36 is typically located remotely from the individual recording devices 32. For example, the analysis server 36 could be located in a different area of a hospital or diagnostic center from the individual recording devices. Alternatively, the analysis server 36 could be located at any remote location and the ECG waveform data can be electronically transferred to the server 36 along the communication line 36. The communication line 36 could be any type of communication network, such as the internet or some hardwired communication technique. The analysis server 36 includes internal processors that are able to carry out the analysis that will be described below. In addition, the analysis server 36 includes the required storage medium such that the ECG waveforms obtained from individual patients through the recording devices 32 can be stored and analyzed as will also be described in detail below.

Figure 3:
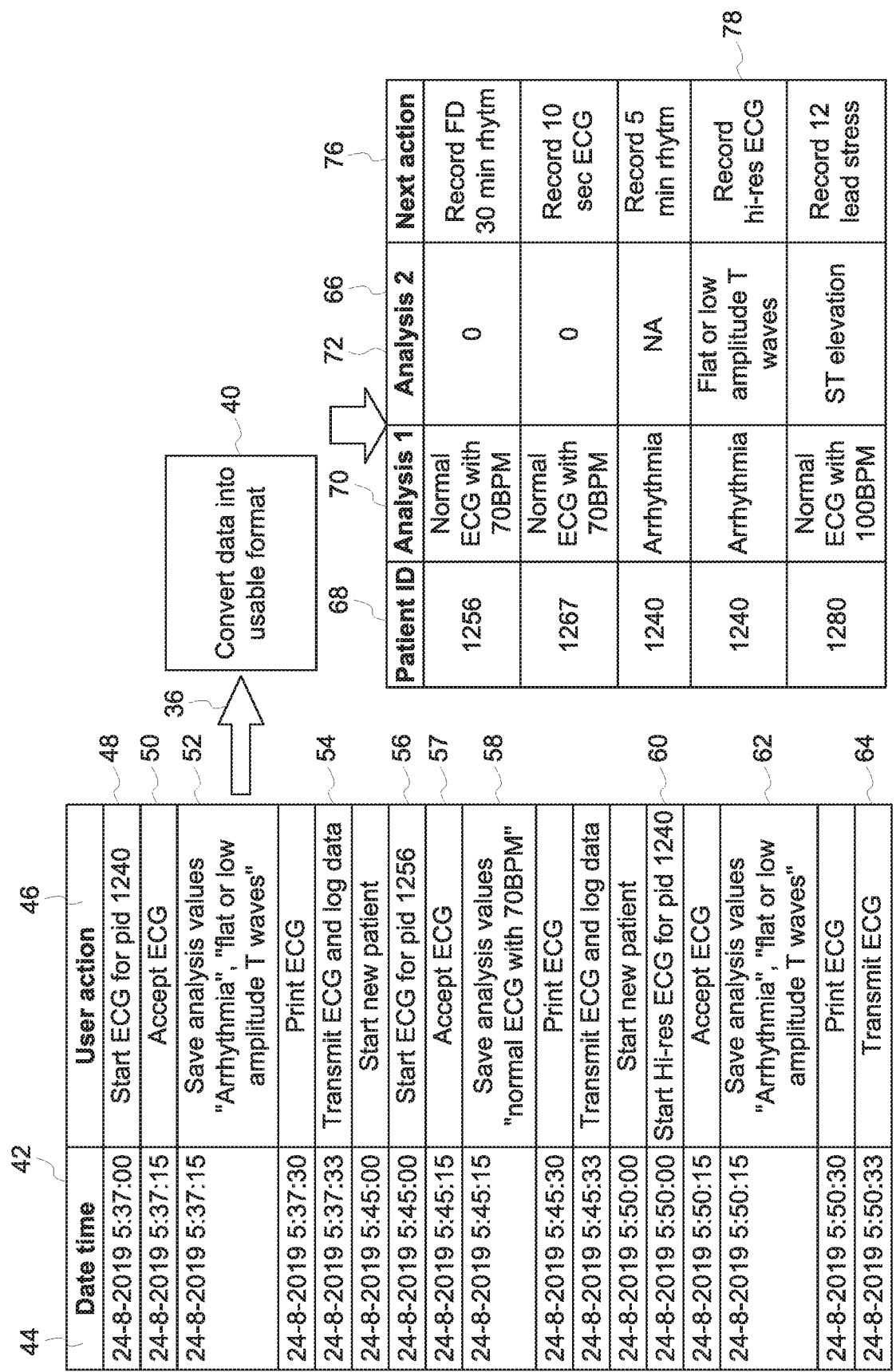
FIG. 3 is a schematic diagram of the receipt of data from multiple patients and the conversion of the data to a form for further processing and analysis.

As illustrated in FIG. 2, after the ECG waveform data has been obtained from the recording device 32 at the analysis server, the analysis server converts the data into a usable format, as illustrated by block 40. Block 40 is further described with reference to FIG. 3. As illustrated in FIG. 3, in addition to the raw ECG waveform data obtained from the recording device, the analysis server also receives a log 42 that provides both a data/time stamp 44 and a description of the type of action taken on the patient, as illustrated the user action column 46.

As illustrated in the first row 48 of the log 42, an ECG was started for patient ID number 1240 at 5:37:00. The user action is thus recorded along with the time of the user action. In row 50, the log 42 indicates that the ECG recording was accepted for patient ID number 1240. After the ECG is accepted, the ECG recording device provides an initial analysis 52, which is saved in the user action column. The initial analysis 52 stored in the user action column indicates that an arrhythmia is present in the ECG waveform data obtained from patient 1240.

The recording device 32 can utilize one of multiple different types of ECG analysis algorithms, such as the proprietary 12SL algorithm utilized by GE Healthcare. The initial analysis carried out by the recording device is stored and transmitted with the ECG data, as indicated by row 54 of the log 52. As can be seen in the first five rows of the log 42, the patient ID number 1240 has obtained an ECG reading, had the reading analyzed by the recording device and the ECG waveform data and log data are transmitted to the analysis server.

Once patient ID number 1240 has completed the initial ECG recording and analysis, the recording device is then used on the next patient having patient ID number 1256 as indicated in row 56 of the log 42. The ECG recording device obtains ECG information from patient ID number 1256, the ECG waveform is accepted in row 57 and the initial analysis is performed by the recording device. In row 58, the initial analysis indicates that the ECG was normal and that the heartbeat for the patient was 70 BPM, as indicated by the user action in row 58.

In row 60, the log 42 indicates that a Hi-Res ECG was performed for the patient ID number 1240 discussed above. As can be understood by the time stamp column, the Hi-Res ECG for patient ID number 1240 occurs approximately thirteen minutes after the initial ECG was taken, as indicated by row 48. The Hi-Res ECG is a recommended action for the patient based on the initial ECG and the recommended action determined by the system and method of the present disclosure, as will be discussed in detail below.

As can be understood by the timing illustrated by the rows in the log 42, the recommended action for the patient occurs very shortly after the initial action. In such situation, the patient has not left the area near the recording device and the second Hi-Res ECG can be obtained without the patient having to visit the cardiologist. In row 62, the recording device again detects that an arrhythmia is present and that the Hi-Res ECG indicates flat or low amplitude T waves are present in the ECG waveform. This analysis is recoded in row 62 and is transmitted, along with the ECG obtained in row 60, to a cardiologist, as indicated by the user action shown in row 64.

As indicated in FIG. 3, the log 42, which includes the date and time stamp as well as information related to the user action and any analysis carried out by the recording device, is sent to the analysis server utilizing the communication line 36. When the log 42 is received by the analysis server, the analysis server carries out the function shown by block 40. In this functional block, the data from the log 42 is converted into a usable format. The usable format for the data contained within the log 42 is illustrated by the summary table 66.

The first column 68 on the summary table 66 provides a patient identification number as was included in the user action column of the log 42. The conversion block 40 pulls the patient identification information form the log 42. The second column 70 provided for the initial analysis that is generated by the operating algorithm on the recording device. As can be understood by the comparison between the summary table 66 and the data log 42, patient 1256 had a normal ECG with 70 beats per minute (BPM). Since the analysis of the ECG was normal, the second initial analysis column 72 is blank. However, for patient ID number 1240, the first initial analysis 70 was the presence of an arrhythmia and the second initial analysis 72 is the presence of flat or low amplitude T waves. Based upon these two initial analyses, the analysis server calculates the next recommended action for the patient, as shown by column 76. For example, based upon the identification of an arrhythmia with flat or low amplitude T waves, the next recommended action proposed is to record a Hi-Res ECG, as indicated by data block 78 in the next action column 76. This next action indicated by block 78 is then transmitted back to the recording device along data communication line 80 shown in FIG. 2.

As indicated by decision block 82 in FIG. 2, after the recording device 32 obtains an ECG recording from the patient, the recording device 32 checks with the analysis server 36 for a recommendation based on the ECG that was recorded. As indicated above, in the next action block 78 shown in FIG. 3, the analysis server generated a recommended action that a Hi-Res ECG is needed for the patient. Since the patient is still present at the recording device 32, the recording device can display the recommended action to the technician in block 84. When the technician receives the directions shown on the recording device 32 in block 84, the technician can then obtain the required ECG from the patient. In the embodiment described, the technician would then obtain a Hi-Res ECG from the patient for further analysis by the cardiologist.

Figure 5:
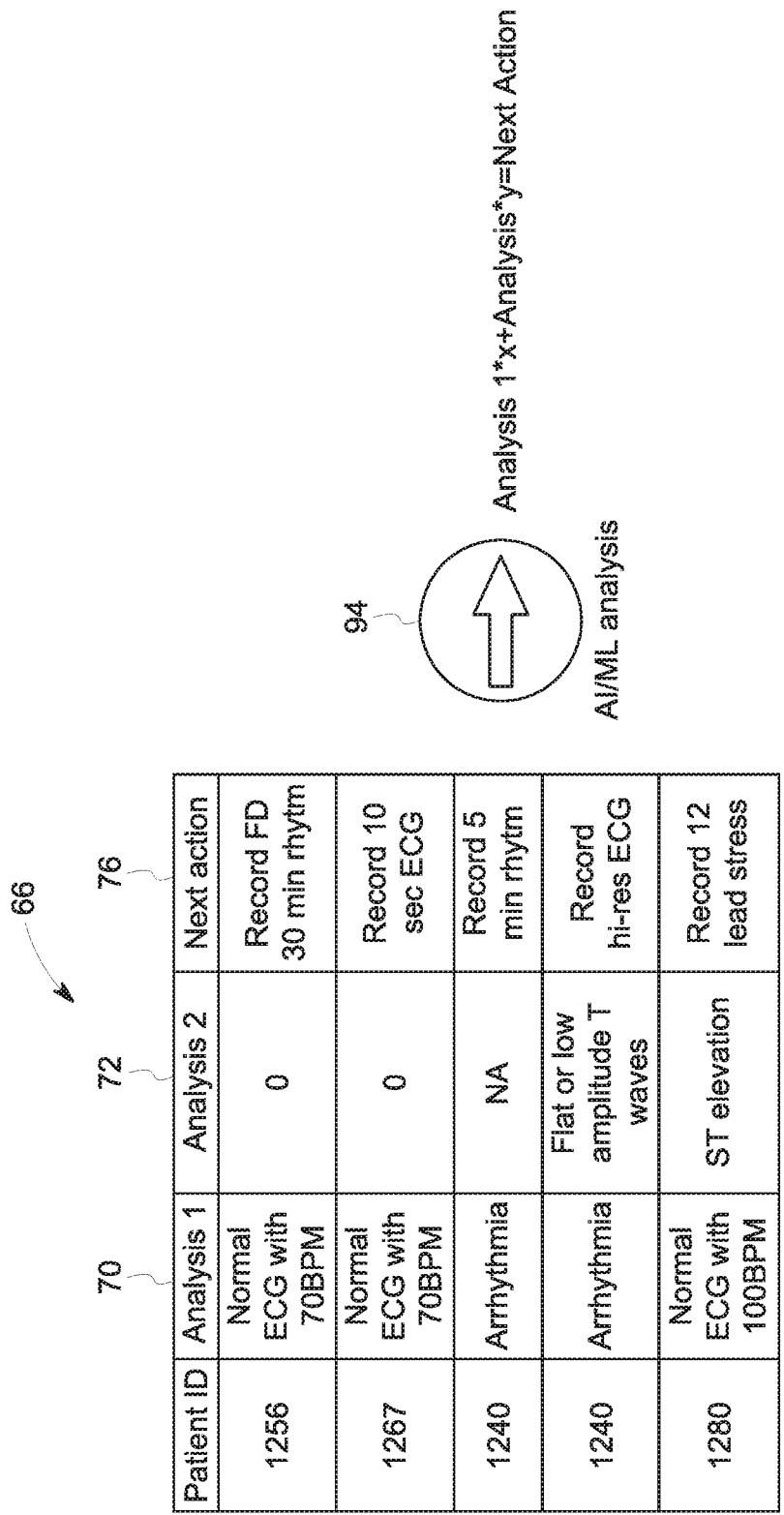
FIG. 5 is a schematic diagram showing the use of artificial intelligence/machine learning in generating a next action based on prior workflows for other patients.

As illustrated in FIG. 2, the analysis server 36 includes a functional block 90 that includes a storage device 92 for receiving and storing both the ECG waveform data and the initial analysis information from each of the recording devices 32. The analysis block 90 further includes a machine learning algorithm 94 that is used as will be described in detail below to generate a recommend action for the patient based upon the first and second analysis information provided from the recording device and based upon prior stored recommendations from previous patients that had similar ECG data and waveforms. The machine learning algorithm 94 indicated by functional block 94 is further illustrated in FIG. 5. The machine learning algorithm 94 shown in FIG. 5 utilizes both the first analysis 70 and a second analysis 72 to create and generate the next action 76. The artificial intelligence/machine learning analysis illustrated by step 94 allows the workflow system and method of the present disclosure to generate a next action that can then be relayed to the technician at the ECG recording device such that the technician can carry out the next action on the patient.

Figure 4:
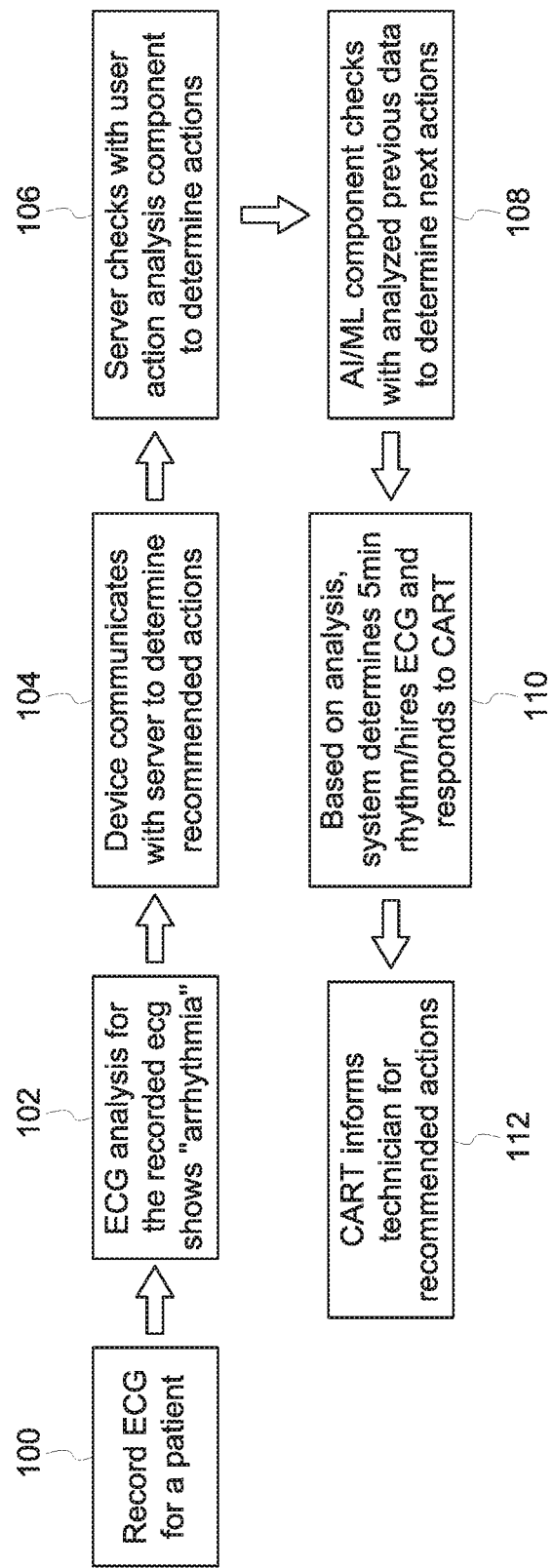
FIG. 4 is a flow chart that depicts an exemplary embodiment of a workflow for the analysis of ECG data obtained from a patient utilizing the analysis method of the present disclosure.

FIG. 4 explains a basic example of the overall workflow in accordance with the concepts of the present disclosure. As shown in FIG. 4, the initial step 100 records the ECG from the patient utilizing one of the recording devices 32. After the initial ECG is recorded, an ECG analysis is carried out in step 102. The ECG analysis carried out in step 102 is carried out utilizing the algorithm present on the recording device 32. As an illustrated example, in block 102 the ECG analysis for the recorded ECG indicates the presents of an arrhythmia. The initial analysis is then recorded in the log 42 shown in FIG. 3 for the patient, along with a date/time stamp.

The workflow in FIG. 4 proceeds to step 104 where the recording device communicates the ECG waveform data and the initial analysis to the server as part of the log. The communication of the ECG information and the initial analysis to the analysis server allows the analysis server to determine the next recommended patient action.

In step 106, the analysis server checks with user action analysis component of the log to determine what should be the next recommended action for the patient. In step 108, the AI/ML analysis component 94 utilizes machine learning along with the analyzed previous data from earlier patients to determine what the recommended next action should be for the patient. In this manner, the machine learning/artificial intelligence algorithm is able to make a recommended action for the patient that can be relayed to the recording device such that the technician can carry out the most relevant action for the patient while the patient is present at the recording device.

In the illustrated example shown in FIG. 4, based upon the analysis carried out in steps 106 and 108, the analysis server determines that a five minute rhythm/Hi-Res ECG is most beneficial for the patient for analyzing the ECG. This analysis and recommended next action for the patient is communicated to the recording device as indicated in step 108. In step 110, the recommended patient action is displayed on the recording device and the technician is able to carry out the action needed. As indicated in detail below, the action taken by the technician can be anyone of multiple different types of ECG recordings for the patient. Such recordings may include a Hi-Res recording, a 15-Lead recording, a 12-Lead recording or any other type of known recordings of ECG information from a patient. Since the patient is still present at the ECG recording device, the recommended action determined by the analysis server can be carried out immediately while the patient is present without having the patient leave the diagnostic center for the analysis and having to return for later ECG recordings.

Figure 6:
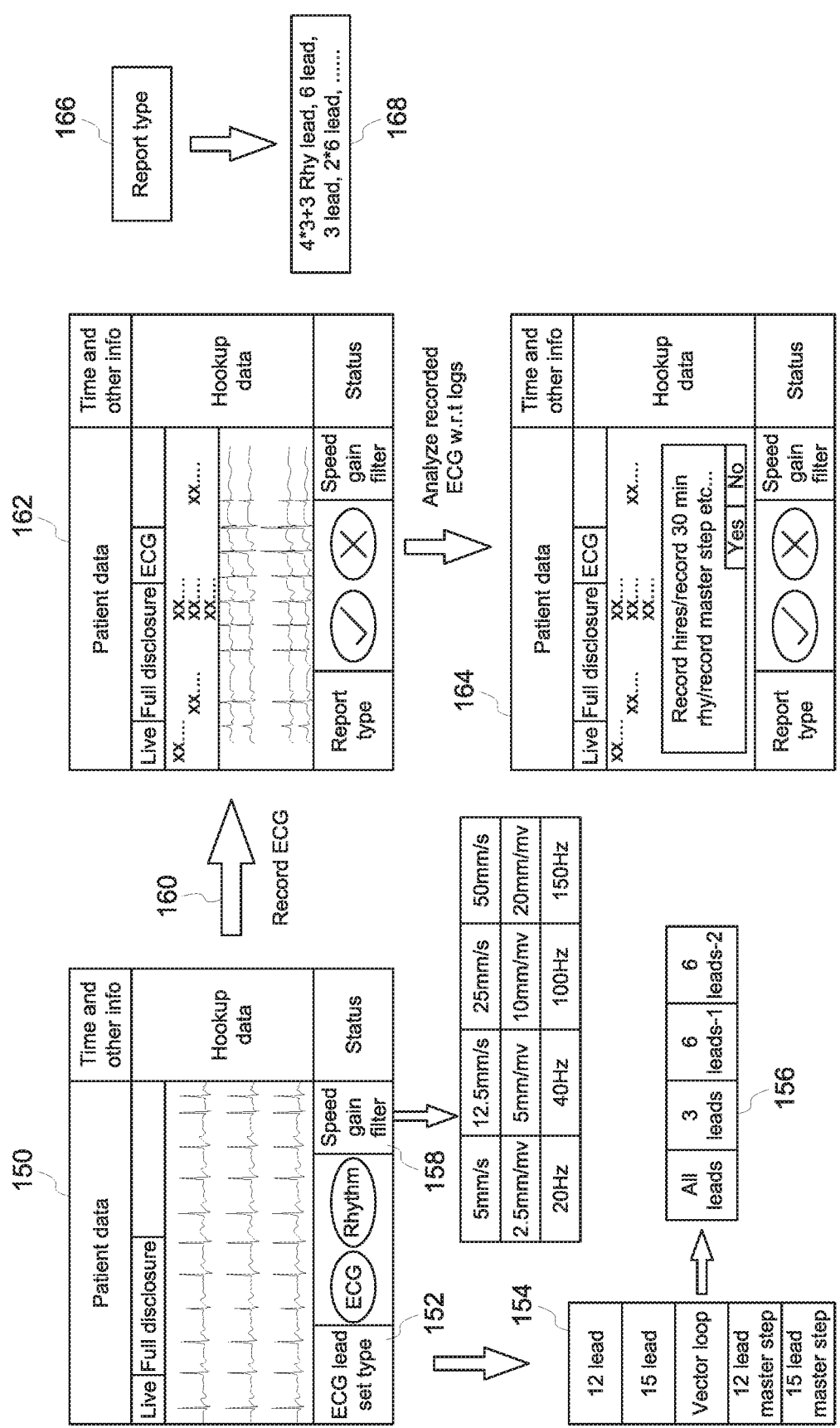
FIG. 6 is a schematic diagram illustrating the types of ECG waveforms and setting that can be configured on the recording device based on the recommended action determined in accordance with the exemplary embodiment.

FIG. 6 presents a graphic illustration of the different types of information that is able to be recorded from a patient utilizing the recording device 32 shown in FIG. 1. The initial display 150 includes various different menu logs that the technician can utilize when recording the ECG information from the patient. As indicated, the ECG Lead set type shown in area 152 allows the technician to select between five different types of ECG measurements indicated by menu block 154. Further, a sub block 156 allows the technician to utilized different combinations of leads applied to the patient.

Menu block 158 allows the technician to select between different speeds, gains, and filters for the ECG information recorded from the patient. Again, the technician can make selections in this menu block based upon the type of ECG to be recorded from the patient.

Based upon the selections from the display 150, the technician can start the recording process as indicated by arrow 160. The ECG waveforms are recorded as shown by the recording block 162. Block 164 illustrates the analysis that can be carried out on the recorded ECG waveform data. A separate report 166 can be generated depending upon the type of information selected by the technician, as indicated by block 168. Since the device Logs contain information about ECG types, reports and settings, an AI/ML recommendation system can utilize this information to provide suggestions to the user about report types and settings to be used for recording the ECG from the patient.

Figure 7:
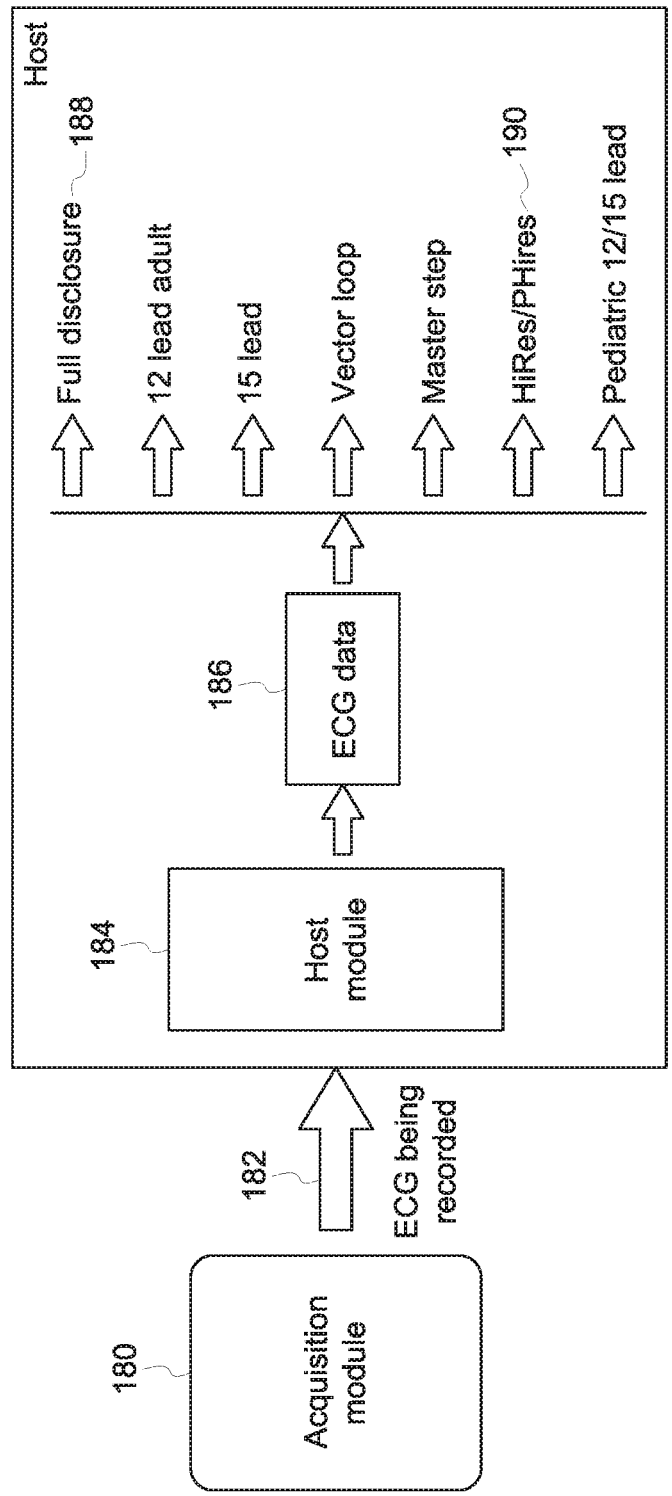
FIG. 7 is a schematic illustration of the types of ECG analysis available for use in carrying out the recommended action.

FIG. 7 further illustrates the various types of ECG data that can be obtained from the patient utilizing the acquisition module 180 of the recording device. The acquisition model 180 obtains ECG information from the patient as illustrated by arrow 182. Some of the ECG data can be obtained from the same recorded ECG information by adjusting the filter/calculation values utilizing the host module 184. The host module 184 is thus able to process the ECG data obtained from the patient to create the processed ECG data 186. The processed ECG data 186 can be utilized to generate various different types of ECG data reports, such as the full disclosure report 188, the Hi-Res report 190 and other types of ECG data thus as illustrated in FIG. 7. The report types shown in FIG. 7 are not limited to those shown and additional report types, such as 12/15 leads stress can also be suggested based on the configuration of the recording device.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of managing workflow during the analysis of ECG waveforms obtained from a patient, comprising:
   sensing an ECG waveform from the patient using a recording device;
   generating an initial analysis at the recording device based on the ECG waveform obtained from the patient by the recording device;
   communicating the recorded ECG waveform and the initial analysis from the recording device to an analysis server;
   analyzing the recorded ECG waveform and the initial analysis at the analysis server;
   determining a recommended action at the analysis server;
   communicating the recommended action to the recording device while the patient is at the recording device; and
   operating the recording device to carry out the recommended action on the patient,
   wherein the recommended action comprises sensing the second ECG waveform, and
   wherein the recommended action comprises sensing the second ECG waveform at a higher resolution or for a longer time period than the initially sensed ECG waveform.

2. The method of claim 1 further comprising the step of displaying the recommended action on the recording device.

3. The method of claim 1 wherein the step of determining a recommended action comprises:
   utilizing machine learning to compare the recorded ECG waveform and the initial analysis to previous patient ECG waveforms and previous patient actions; and
   generating the recommended action based on the machine learning analysis.

4. The method of claim 3 further comprising the step of communicating the recommended action from the analysis server to the recording device while the patient is at the recording device.

5. The method of claim 3 further comprising the step of recording the recommended action and the ECG waveform at the analysis server.

6. The method of claim 5 wherein the machine learning utilizes the recorded recommended actions to determine the recommended action.

7. The method of claim 5 wherein the recommended action includes generating a selected report from the ECG waveform.

8. The method of claim 1 wherein the recommended action is determined based on the initial analysis.

9. A method of managing workflow to analyze an ECG waveforms obtained from a patient, comprising:
   sensing an ECG waveform from the patient utilizing a recording device while the patient is present at the recording device;
   generating an initial analysis at the recording device of the ECG waveform obtained from the patient by the recording device;
   communicating the recorded ECG waveform and the initial analysis from the recording device to an analysis server;

analyzing the recorded ECG waveform and the initial analysis at the analysis server;

determining a recommended patient action at the analysis server;

storing the recommended patient action, the initial analysis and the ECG waveform at the analysis server;

communicating the recommended patient action to the recording device while the patient is at the recording device; and operating the recording device to carry out the recommended patient action on the patient, wherein the recommended action comprises sensing a second ECG waveform, and wherein the recommended action comprises sensing the second ECG waveform at a higher resolution or for a longer time period than the initially sensed ECG waveform.

10. The method of claim 9 further comprising the step of displaying the recommended patient action on the recording device.

11. The method of claim 9 wherein the step of determining a recommended patient action comprises:

utilizing machine learning to compare the recorded ECG waveform to previous patient ECG waveforms and previous patient actions; and generating the recommended patient action based on the machine learning analysis.

12. The method of claim 11 further comprising the step of communicating the recommended action from the analysis server to the recording device while the patient is at the recording device.

13. The method of claim 11 wherein the machine learning utilizes the recorded recommended patient actions to determine the recommended patient action.

14. The method of claim 11 wherein the recommended patient action includes generating a selected report from the ECG waveform.

15. The method of claim 11 wherein the recommended patient action includes adjustments to the recording device.

16. The method of claim 11 wherein the recommended patient action includes the selection of a selected report type.

17. A method of managing workflow during the analysis of ECG waveforms obtained from a patient, comprising:

sensing a first ECG waveform from the patient using a recording device;

generating an initial analysis at the recording device based on the first ECG waveform obtained from the patient by the recording device;

communicating the recorded first ECG waveform and the initial analysis from the recording device to an analysis server;

receiving, by the recording device while the patient is at the recording device, a recommended action generated by the analysis server based on an analysis of the first ECG waveform and the initial analysis; and operating the recording device to carry out the recommended action on the patient, wherein the recommended action comprises sensing a second ECG waveform, wherein the recommended action comprises sensing the second ECG waveform at a higher resolution or for a longer time period than the first ECG waveform.

* * * * *